United States Patent [19]

Boebel

[11] 4,273,129
[45] Jun. 16, 1981

[54] FORCEPS FOR APPLYING CLIPS TO FALLOPIAN TUBES

[75] Inventor: Manfred Boebel, Oetisheim, Fed. Rep. of Germany

[73] Assignee: Richard Wolf GmbH, Knittlengen, Fed. Rep. of Germany

[21] Appl. No.: 50,454

[22] Filed: Jun. 20, 1979

[30] Foreign Application Priority Data

Jun. 29, 1978 [DE] Fed. Rep. of Germany ....... 2828564
Dec. 27, 1978 [DE] Fed. Rep. of Germany ....... 2856241

[51] Int. Cl.³ .............................................. A61B 17/12
[52] U.S. Cl. ............................... 128/326; 227/DIG. 1
[58] Field of Search ............... 128/325, 321, 346, 326, 128/334 R; 72/410; 29/243.56; 227/1 B

[56] References Cited

U.S. PATENT DOCUMENTS 3,954,108  5/1976  Davis .................................... 128/325

FOREIGN PATENT DOCUMENTS 251138  1/1970  U.S.S.R. .................................. 128/754

Primary Examiner—Robert W. Michell
Assistant Examiner—Michael H. Thaler
Attorney, Agent, or Firm—Kinzer, Plyer, Dorn & McEachran

[57] ABSTRACT

This invention relates to forceps for applying a clip to a Fallopian tube. The clip is in one piece and made of a somewhat flexible plastics material. It has two separable arms which are connected by a flexible strip: one of these arms has a catch recess in a free end thereof to face the strip, into which recess the end of one of said spring arms is pressable by elastic deformation.

According to the invention the forceps have an outer shaft to receive the clip open in a distal cut-out with the straight arm extended; the forceps additionally comprise two proximal handle members for opening and closing and consisting of a pivotally arranged two-armed closing lever. One arm of this closing lever has a distal flat face flush with the outer shaft so the forceps may be inserted through an outer trocar tube. Abutting against the straight clip arm and proximally in front of it is a projection; the other arm of the two-armed lever is pivotally connected to a rod which is axially stopped with respect to the pivot bearing of the closing lever by a proximal handle members and is distally movable and then is distally movable with the pivot bearing so that the projection of the closing lever becomes aligned against the straight clip arm and so that, by leaving the closing lever bearing in position, the rod is proximally movable to close the clip.

11 Claims, 11 Drawing Figures

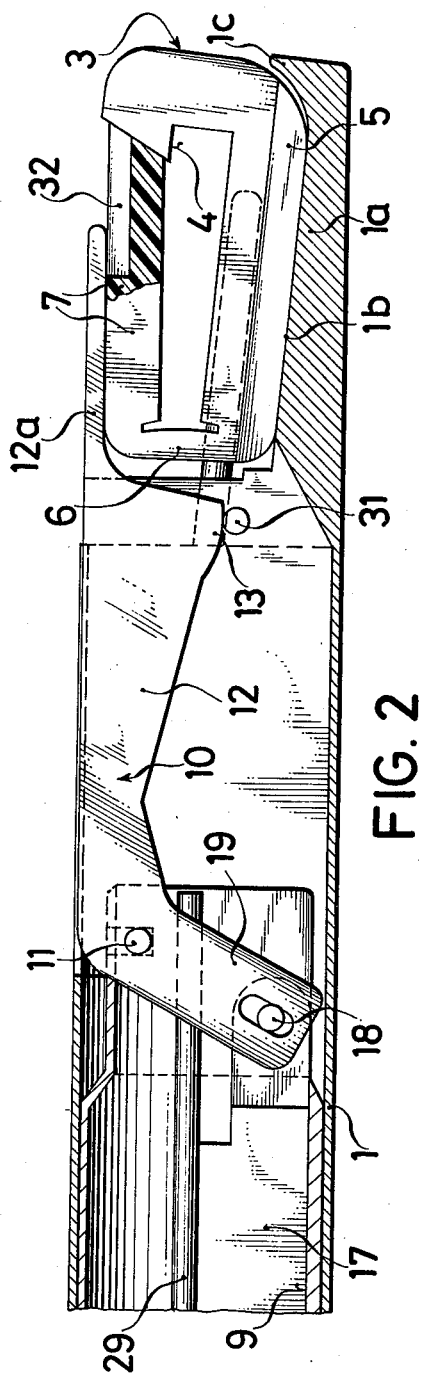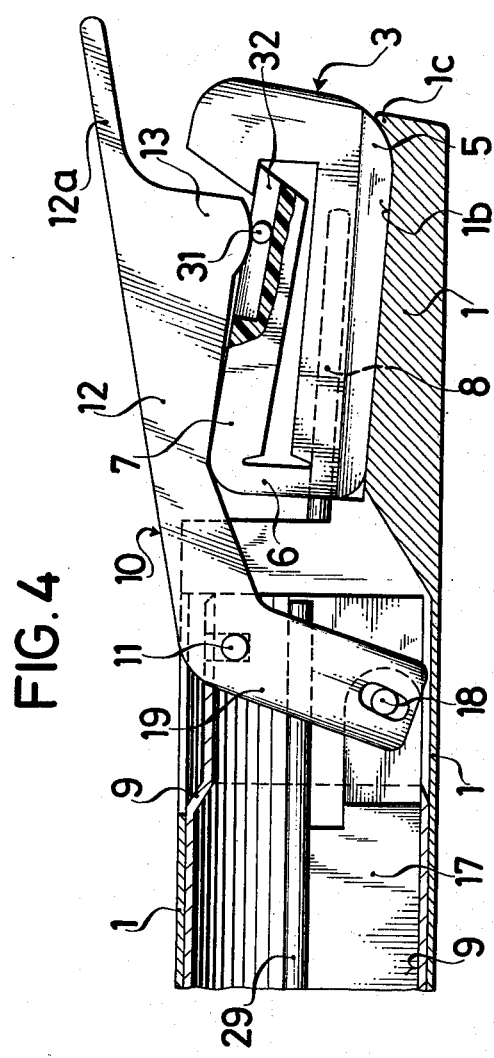
FIG. 2
FIG. 4

FORCEPS FOR APPLYING CLIPS TO FALLOPIAN TUBES

BACKGROUND OF THE INVENTION

The present invention relates to forceps for applying clips to fallopian tubes, said clip being in one piece clip and made of a somewhat flexible plastics material and having two separable arms which are connected by a flexible strip, one of said arms having a catch recess in a free end thereof facing said strip, into which recess the end of the other one of said spring arms is pressable by elastic deformation.

It is an object of the invention to provide means for the application of clips of the above mentioned type to fallopian tubes simply and correctly by the doctor by means of an instrument to be inserted into the abdominal cavity through a trocar tube instead of by a simple cutting forceps, as described for example in German Patent Specification No. 1 957 855, the fallopian tubes being closed off by pressing the two arms of the clip together.

SUMMARY OF THE INVENTION

Accordingly, the invention consists in a forceps for applying a clip to a fallopian tube, said clip being a one piece clip and made of a somewhat flexible plastics material and having two separable arms which are connected by a flexible strip, one of said arms having a catch recess in a free end thereof facing said strip, into which recess the end of the other one of said spring arms is pressable by elastic deformation, said forceps having an outer shaft to receive the clip distally open in a distal cut-out with the straight arm extended and said forceps comprising two proximal handle members for opening and closing and consisting of a pivotally arranged two-armed closing lever one arm of which has a distal flat face flush with said outer shaft so the forceps may be inserted through an outer trocar tube and abutting against said straight clip arm and proximally in front of it there is a projection and the other arm of which is pivotally connected to a rod which is axially stopped with respect to said pivot bearing of said closing lever by said proximal handle members and is distally movable and then is distally movable with said pivot bearing so that said projection of said closing lever is aligned against said straight clip arm and so that, by leaving the closing lever bearing in position said rod is proximally movable to close the clip.

By proximal manipulation it is thus possible by opening the closing lever to insert the clip into the distal end of an outer shaft of the forceps, then to partly close the closing lever, so as loosely to position the straight clip arm against the other hooked arm of the clip by the means of the flat face of the closing lever so as thus to leave the straight arm flush with the outer shaft thus to be able to insert the instrument with the engaged clip through a trocar tube. The forceps are opened again or the closing lever is opened so that the clip also opens due to its own elasticity so that it can be pushed over the Fallopian tube and the clip can then be closed round the Fallopian tube by pressure exerted by the closing lever projection against the straight clip arm. The operation is thus completed and the instrument can be withdrawn, leaving the clip attached to the Fallopian tube.

To avoid the doctor having to manipulate against a spring action on fixing the clip on the Fallopian tube, the forceps handle which is rigidly connected with the outer shaft extension preferably has a two armed ring lever fitted with a spring, one arm of which is positioned through a slot in the shaft extension behind a ring flange of the inner shaft which moves in distal direction against its spring action. Thus the swivel bearing of the closing lever automatically remains in the distally advanced position and moreover the closing lever can however be open or closed as will be explained later so that the doctor's work is largely facilitated.

BRIEF DESCRIPTION OF THE DRAWINGS

In order that the invention may be more clearly understood, reference will now be made to the accompanying drawings which show one embodiment thereof by way of example and in which:

FIGS. 2, 3, 4 show the distal somewhat further enlarged part of the clip forceps of FIG. 1 in three different positions of the closing lever, FIG. 5 is a cross-section through an opened clip in the distal end of the outer shaft.

DETAILED DESCRIPTION OF THE PREFERRED EMBODIMENT

Figures 3, 5:
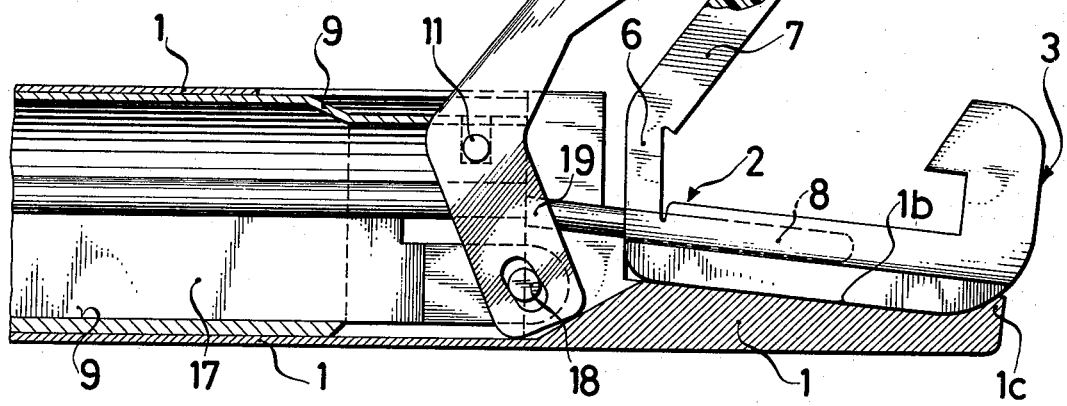

Referring now to the drawings, in the embodiment shown, an outer shaft 1 is provided with a cutaway portion 2 at the distal end the remaining distal part of the outer shaft being thickened, is flat on the upper side 1b and has a protruding lip 1c at the distal end. The distal end of the instrument is the end farthest from the hand of the surgeon; the proximal end is nearer the surgeon. The clip 3 is slid along the base 1b as shown in FIG. 5. The clip 3, which is made of somewhat flexible plastics material, consists of a lower arm or blade 5 which is T-shaped with a hooked recess or notch 4, and the blade 5 is connected by a flexible strip 6 (FIG. 2) to a straight arm 7 whereby the strip 6 causes the opening of the straight arm 7 or the automatic opening of the clip. The clip 3 is held by the lip 1c in the distal direction. So as not to lose it under any circumstances after insertion, the distal shaft end has a small knob 8 on both sides which catches in the flange of the clip arm 5 and thus holds the clip fast (FIG. 5).

An inner shaft 9 runs through the outer shaft 1 and has a two-armed closing lever 10 pivotally mounted on shaft 9 at 11 at its distal end. The one lever arm 12 ends in a flattened straight end 12a and so that it can be brought into a position flush with the outer shaft 1. The arm 12 is provided at the underside with a projection 13 proximally of the flattened end 12a. The inner shaft 9 ends proximally in a cylindrical extension 1a of the outer shaft and has a flange 15 biased by a pre-tensioned spring 14 in proximal direction against a fixed step 16.

An operating rod 17 runs through the inner shaft 9, the distal end of said rod being articulated to the other arm 19 of the closing lever 10 at 18. This rod 17 is rigidly connected proximally with a guide 20 slidably fitted inside the shaft extension 1a. The free end, for example the forked end, of the one arm 22 of the forceps handle 23 which is pivoted to the handle 25 at 24, catches in a notch 21 of the guide 20 through a lower longitudinal slot of the outer shaft. This latter handle 25 is rigidly connected with the outer shaft or outer shaft extension 1a.

Figure 1:
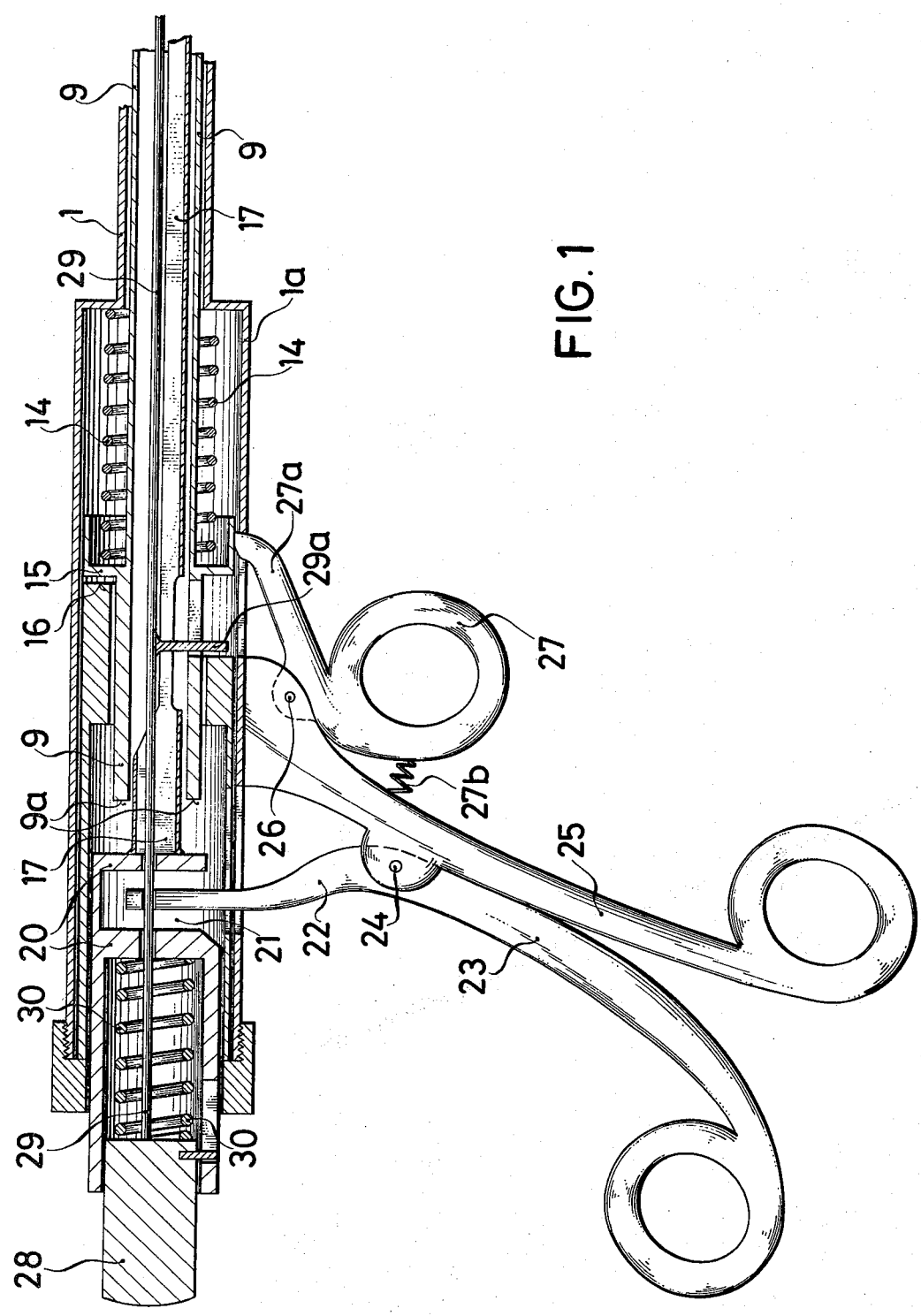
FIG. 1 shows the proximal part of the clip forceps in axial section to an enlarged scale.

The forceps described operate as follows:

Starting from the rest position of the parts according to FIGS. 1 and 2 the handle arm 22 moved a little in distal direction by moving apart the handles 23 and 25, also taking along the guide 20 and the rod 17 as well in the distal direction. This is possible as the guide 20 in its rest position is at a distance from the proximal end 9a of the inner shaft. The inner shaft 9 with the distal swivel bearing 11 of the closing lever 10 at first therefore remains in position as the guide 20 still has not reached the proximal end 9a of the inner shaft 9. Thus the closing lever 10 is opened, as it is swung round by the rod 17 which is moving forward. Now the clip 3 can be distally inserted (see FIG. 3) in the way described.

Next the forceps handle 23 is again returned to its rest position as in FIG. 1 whereby the guide 20 and thus the rod 17 are moved in proximal direction which now distally moves the closing lever 10 into the position shown in FIG. 2 in which only a flattened distal part 12a of the closing lever is positioned against the clip arm 7 whereby the closing lever is flush with the outer shaft. The clip arm 7 is thus still not in any position however in which the end of the arm is pressed behind the hook notch 4 of the other clip arm 5, i.e. the clip is still unlatched. In this position (FIG. 2) the entire forceps and the clip in it can be inserted into the abdominal cavity through a trocar tube.

After insertion into the abdominal cavity the closing lever 10 is again moved into the open position by again separating the forceps handles 23 and 25 and thus by distal moving of the rod 17 whereby the clip automatically opens due to its own elasticity so that it can now be positioned over the Fallopian tube. As soon as this is accomplished the guide 20 is next positioned against the end 9a of the inner shaft 9 by opening the handles farther and thus the inner shaft 9 together with the rod 17 is moved in this direction i.e. both pivot points 11 and 18 are moved in distal direction when the closing lever 10 is opened and thus the projection 13 of the lever arm 12 reaches the area of the flat clip arm 7 (FIG. 3). On the distal movement of the inner shaft and the rod 17 a hand lever 27 pivotally mounted on the handle 25 at 26 engages with the end of the lever arm 27a through a slot in the extension (1a) behind the stop flange 15 of the inner shaft 9 by pressure of the spring 27b the position of which is thus fixed. Due to this fixing the doctor no longer needs to overcome the force of the spring 14 so that he is in a position to move the clip freely over the Fallopian tube.

The handle 23 is then returned under pressure to the position shown in FIG. 1, the pivot axis 11 and the inner shaft 9 however maintaining their distal position while the rod 17 is moved in proximal direction and thus takes the pivot 18 with it so that the closing lever arm 12 is now positioned under pressure with the projection 13 against the clip arm 7 and thus the end of the arm 7 is pressed under elastic deformation behind the hook notch 4 so that the Fallopian tube is thus encircled and compressed by the clip.

The closing lever arm 12 is then removed again from the clip 3 by slight separation of the handle 23 and now the clip is removed from the jaw of the forceps and is retained on the Fallopian tube. To facilitate this the guide 20 of the operating rod 17 is in the form of a cylinder in which is fitted a proximally limited spring-loaded piston 28. A push rod 29 is connected with this piston 28, and as soon as the piston 28 is pressed against its spring 30 in the distal direction into the cylinder by thumb the push rod 29 is taken along with it and its distal end is positioned against the strip 6 of the clip 3 (see FIG. 2) thereby pushing the clip from its support base 1b in the distal direction. At the same time the pin 29a engages and frees the hand lever 27a which previously engaged behind stop flange 15 and upon slowly freeing the piston 28 it slides back to the starting position as shown in FIG. 1. The push rod 29 at the same time freely penetrates the guide 20 and is guided through the inner shaft parallel to the operating rod 17.

If a clip which has already been inserted into the abdominal cavity by the forceps has not been applied for some reason, fixing of the inner shaft 9 is stopped by manual operation of the hand lever 27. The inner shaft 9 and the rod 17 return to the starting position as shown in FIGS. 1 and 2 thus ending the operation.

Under certain circumstances it can be advantageous to usefully open the straight arm 7 of the clip on opening the closing lever arm 12 in case the inherent elasticity of the clip is proportionally weak at the strip 6. For this purpose the projection 13 of the closing lever arm 12 may be provided with a ball head 31 which engages with a distally open undercut groove 32 (FIG. 3) of the clip lever 7 which can thus be opened wide so as the Fallopian tube and close in the right direction without problems.

In FIGS. 1 to 5 the removal of the clip 3 fastened round the Fallopian tube can be made by hand operation of the piston 28. To facilitate the doctor's removal of the closed clip he can proceed as follows according to the embodiment in FIGS. 6 to 7b. For this purpose forceps handles 23, 25 are used which, in the rest position of the forceps, are forced apart by a spring 23a the forceps shanks 22 and 25a then being co-adjacent or practically so. The part 25, 25a is again rigidly connected with the extension 1a of the forceps shaft and the arm 22 of the jaws engages like a joint in fork fashion in the distal space 21 of a displaceable guide 20 for a piston 28 spring-urged in the proximal direction by spring 30, and with push rod 29. The guide 20 for the piston 28 is fixedly connected on the distal side again with a push rod 17 which articulatedly and distally engages with the one arm of the pivotal forceps jaw arm.

The aim of the invention is to obtain the removal of a closed clip encircling Fallopian tube easily and comfortably from the forceps.

For this purpose a release device is screwed as a unit onto the proximal end of the shaft extension 1a. The unit consists of a cylindrical housing 33 which is screwed onto the shaft extension by a thread interiorly of a distal shoulder thereof. In this housing 33 is located at hollow cylinder 34 which is axially displaceable against a spring 35 loosely against the proximal front end of the guide 20. The hollow cylinder 34 has an inner flange 34a against which on the one hand the piston 28 is positioned by its pre-tensioned spring 30 and which on the other hand supports the one end of the spring 35. A sleeve 36 which receives the head of a screw 37 which is screwed into the base 33a of the housing 33 which supports the other end of the spring 35 is screwed into the flange 34a whereby the sleeve 36 and the screw 37 prevent the hollow cylinder 34, on being screwed off in the direction of release, from falling out of the housing 33 and thus the stopper balls 47 can also remain in position.

On the outer periphery of the housing 33 are mounted one after the other adjacent to the distal end of the housing a compression spring 38, a cylinder ring 39 with a 90 degree cut away section 38a, the sloping face 39b of which abuts against a mini ball bearing 40 which is fixed in the housing 33, and at the sloping face 39c of which the lip 41a a rotatable ring 41 moves, the slope 41b of the lip 41a facing the sloping face 39b of the ring 39 being parallel to this i.e. less than 45 degrees. Parts 38, 39 and 41 have the same outer diameter as the distal flange of the housing 33 so that a rotatable outer sleeve 42, the flange 42a of which abuts against the ring 41, can be displaced over this unit. The outer sleeve 42 and the ring 41 are fixedly connected together by a trunnion screw 43, the trunnion 43a of this screw penetrating into a cross slot 44 of the housing 33 and thus fulfilling a stop function.

Figures 6, 6A:
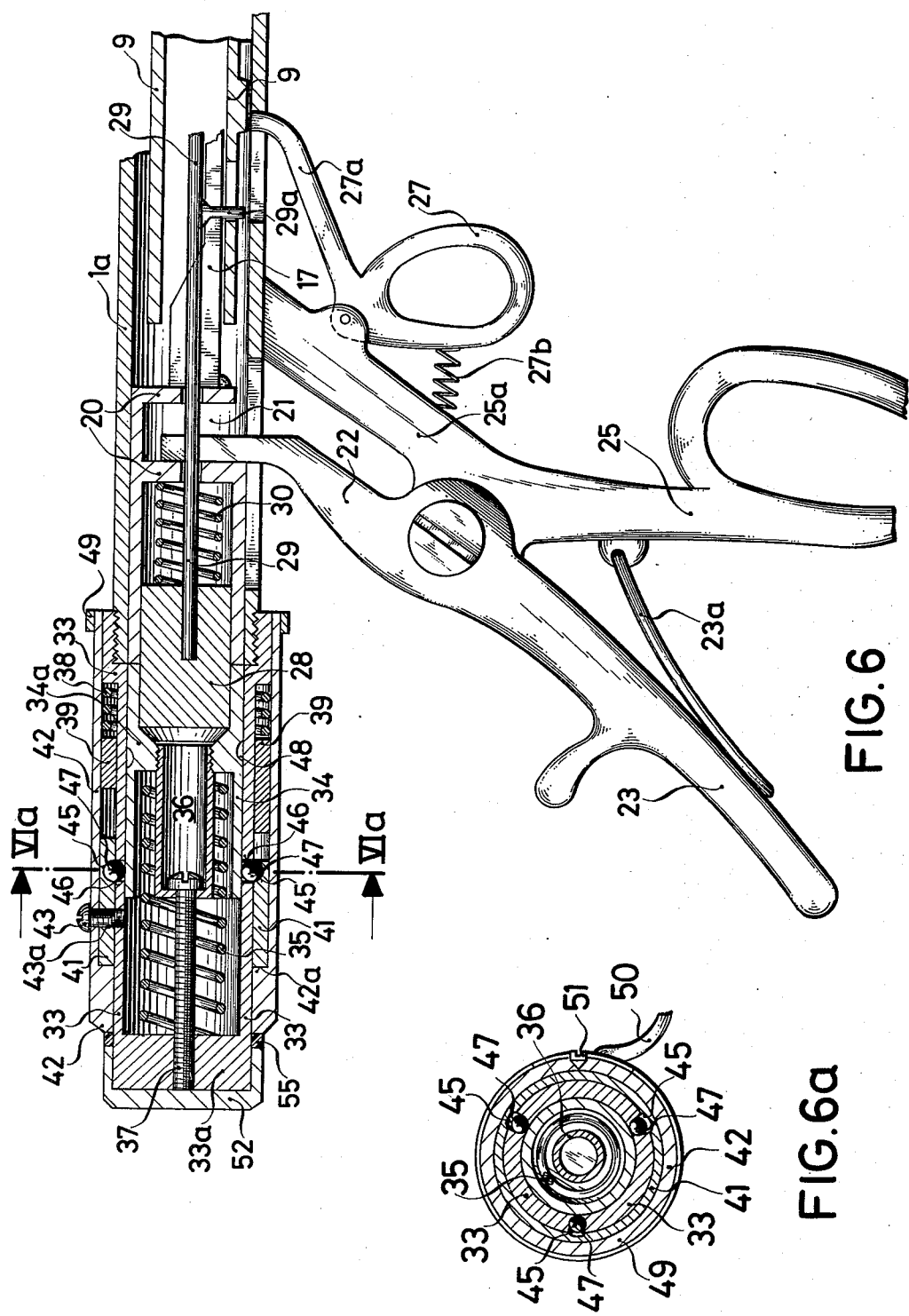
FIG. 6 is an axial section along the axis through the proximal end of the shaft extension of the forceps as shown in FIG. 1 with an improved release device for the injection of a closed clip from the forceps mouth in its rest position.
FIG. 6a is a cross-section along the line VIa—VIa of FIG. 6.
Figure 6B:
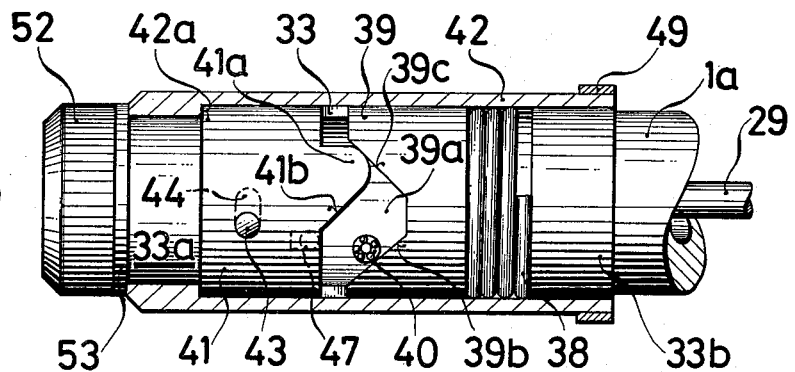
FIG. 6b is a view of a release device with the outer sleeve cut away.
Figure 7:
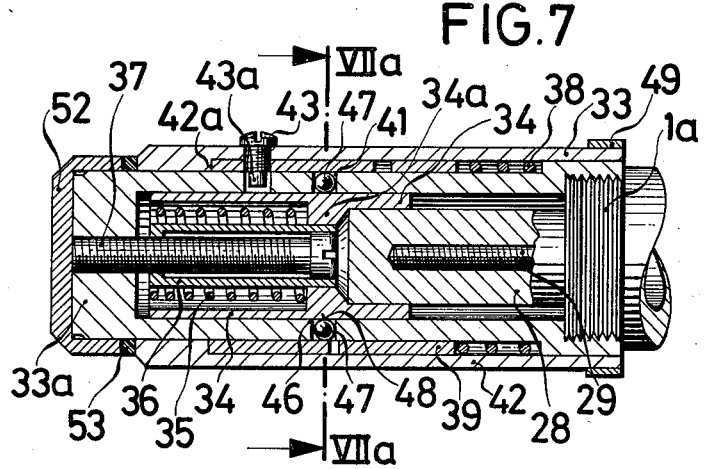
FIG. 7 is an axial section corresponding to FIG. 6 with a tensioned release device.
Figure 7A:
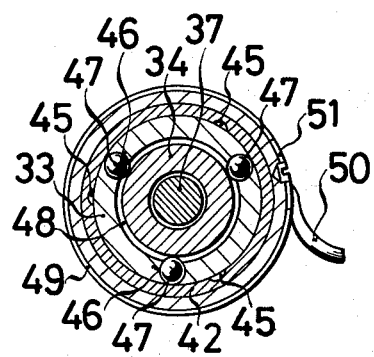
FIG. 7a is a cross-section along the line VIIa—VIIa of the FIG. 7.
Figure 7B:
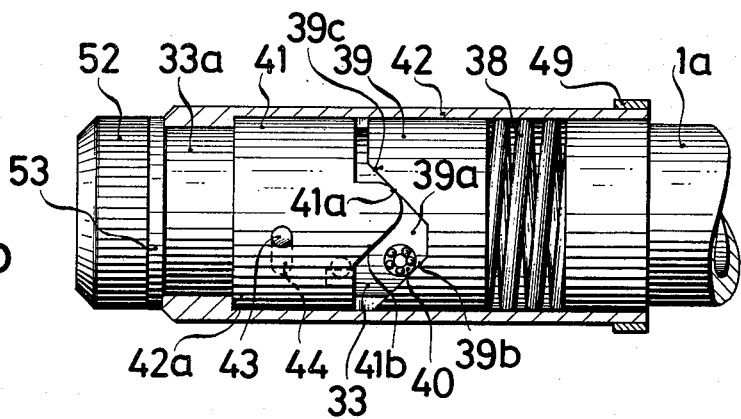
FIG. 7b is a view of the embodiment according to FIG. 7 with the outer sleeve cut away.

The ring 41 at equal distances axially over the length of its inner circumference has three ball-shaped grooves or recesses 45 in which engage three stopper balls 47 mounted in the facing bores 46 of the housing, whereas the balls lie or slide on the other hand on the outer circumference of the hollow cylinder 34 (FIGS. 6 and 6a). The hollow cylinder 34 is provided with a circular slot 48 in the distal direction at a distance from the above described position of the ball bearing 47 corresponding to the stroke h of piston 28 which still has to be described (FIGS. 6, 6a, 7a).

Distally at the connection side of the shaft extension 1a, a ring 49 with a finger-controlled lever or key 50 encircles the outer sleeve 42 which is fixed in position on the outer sleeve 42 by a small set screw 51 to suit requirement conditions. A round head screw 52 proximally forms the connection with the release device which is screwed onto the base 33a of the housing and is pressed against a slip ring 53 abutting on the front face of the outer sleeve flange 42a and advantageously made of "Teflon" (Registered Trade Mark) or the like.

The device operates as follows: Before placing a clip in the opened jaws of the forceps as in FIGS. 1 to 7 the handles 23, 25 are pressed together so that the shanks 22 of the jaws deviate in the proximal direction and take the guide 20 with them. Thus the hollow cylinder 34 is also brought proximally against the spring 35 until it is positioned approximately against the base 33a of the housing 33. The rod 29 of the piston 28 follows the movement of the hollow cylinder 34 due to the pre-tensioned spring 30.

On proximal sliding of the hollow cylinder 34, the balls 47 slide axially on the periphery of the hollow cylinder 34 until they engage in the peripheral groove 48 of the hollow cylinder 34 due to the radial movement of the ring 41 and thus execute a radially inwards movement. The radial movement of the ring 41 is brought about by a spring 38, the ring 39 and ball bearing 40. By displacement of the ring 41, the balls 47 are pressed into the peripheral groove 48 of the hollow cylinder 34 and lock this in position.

The rotating ring 41 takes with it via screw 43 the outer part 42 which is provided with the finger-operated lever or key 50 the shank 43a of the screw 43 moving in the slit 44 of the housing 33.

Then the handles 23, 25 are freed so that they are parted by the spring 23a the guide 20 moving with them to open the right arm of the forceps via rod 17. Then the clip is inserted into the forceps jaws and thereby the pivoted forceps shank is brought into flush alignment with the inner shaft of the forceps so that the forceps and the clip can be inserted into the abdominal cavity through a trocar tube after tensioning of the release device and closing the handles. The insertion of the clip into the forceps should be made after tensioning of the clip device as described for FIGS. 1-5.

If the clip is pushed over the Fallopian tube and closed by the forceps the doctor can turn the outer sleeve 42 and the ring 41 in the other direction by simply actuating the lever or key 50. Thus the fluted grooves 45 are positioned over the stopper balls 47; the balls are pressed out of the circular groove of the hollow cylinder 34 by pressure of the spring 35 and the hollow cylinder 34 is then pushed distally by the tensioned-spring 35, taking the piston 28 and the rod 29 with it, through the distal end of which rod the clip is pushed out of the opened jaws of the forceps.

I claim:

1. Forceps for applying a clip to a fallopian tube, said clip being in one piece and made of plastics material and having two separable arms connected by a flexible strip, one of said arms having a latch recess in a free end thereof facing said strip, into which recess the end of the other one of said clip arms is pressable by elastic deformation, said forceps having an outer shaft provided with a cutout to receive the clip in open condition with the other clip arm extended, said forceps comprising two proximal handle members for relative opening and closing movement, a two-armed closing lever mounted for opening and closing movement on a pivot bearing carried by a movable inner shaft inside said outer shaft, one arm of said lever when closed having a face parallel with said outer shaft to lie adjacent said other clip arm when the clip is closed, the one lever arm also having a projection engageable with the other clip arm when in the open condition to press it into said latch recess to latch the clip and the other lever arm being pivotally connected to a lever-operating rod movable axially inside said outer shaft both in the distal and proximal direction upon movement of said proximal handle members, and means to advance said inner shaft and pivot bearing distally with said rod after the latter has first been moved distally a predetermined distance, whereby said rod upon movement of said handle members first is distally movable through said predetermined distance to open said closing lever and then is distally movable farther to simultaneously advance said inner shaft and said pivot bearing distally so that said projection of said closing lever is aligned against said other clip arm and so that, by leaving the closing lever in said aligned position said rod may be retracted proximally to cause said lever to close the clip.

2. Forceps according to claim 1, wherein said movable inner shaft has, at its distal end, said pivot bearing of said closing lever and, in a proximal extension of said outer shaft, is spring-urged proximally up to a stop, and wherein said rod for said closing lever passes through said inner shaft and is connected proximally at a distance from the proximal end of said inner shaft to a rod guide in said outer shaft extension, one of said handle members having a shank which goes through a slot in said outer shaft and is engageable with said guide for said rod, and the other of said handle members being rigidly connected with the outer shaft extension.

3. Forceps according to claim 2, including spring means to bias the inner shaft in the proximal direction whereby said spring means is compressed during distal movement of the inner shaft, and wherein said forceps handle which is rigidly connected to said outer shaft extension has a two-armed spring-loaded finger grip, one arm of which is positioned through a slot in said outer shaft to engage behind a flange of said movable inner shaft to hold the latter against its spring loading upon latching the clip.

4. Forceps according to claim 2, wherein said guide for said operating rod for activating said closing lever is constructed as a cylinder in said outer shaft extension, in which cylinder is displaceably located a piston which is proximally spring-urged and which protrudes in limited fashion therefrom, said piston being connected to a push rod passing freely through said inner shaft, said push rod being positionable by finger pressure on said piston against the closed clip for its ejection from said forceps.

5. Forceps according to claim 4, wherein that said push rod is provided with a pin which presses said one lever arm of said hand lever from its latched position for the purpose of returning said forceps to the initiating position.

6. A release device for releasing a clip for closing off a Fallopian tube combined with a forceps according to claim 4, said guide for said piston being positioned in a cylinder housing mounted on the proximal end of said shaft extension, the proximal end of said guide engaging loosely against the facing end of a distally spring-urged hollow cylinder having a flange which accommodates the crown of said piston as a stop, and wherein said hollow cylinder is pressed against a proximal stop by compression of a spring by said guide by actuation of said forceps handle, and for this position an automatic locking mechanism which is releasable by slight pressure on a lever or key is provided.

7. A device according to claim 6, wherein the cylinder housing is screwed onto the shaft extension, said device having an outer rotatable sleeve surrounding said cylinder housing, and wherein two axially spaced cylinder rings are mounted between the outer circumference of said cylinder housing and said outer sleeve, of which the ring on the distal side is stressed in the proximal direction by a spring and on a proximal interface thereof has a sliding edge inclined in the axial direction at which a lip of the other cylinder ring is engaged, said rotatable sleeve having an exterior key or lever, said other ring being rotatable and being provided on the inner circumference with longitudinal recesses receiving stopper balls mounted in radial bores of said housing and which abut on the other side against the circumference of said hollow cylinder, said hollow cylinder being provided with a circular groove in which said stopper balls engage in the tensioned position of said hollow cylinder under localized rotation of said outer rotatable sleeve.

8. A device according to claim 7, wherein said outer rotatable sleeve is provided with an external operating lever or key rigidly connected to said cylinder on the proximal side by a screw which screw has a shank end in a transverse slot of said housing.

9. A device according to claim 8, wherein a ring is attached to the distal peripheral end of said sleeve said ring having an operating lever or key for rotating the jaws of said forceps and said cylindrical ring connected therewith.

10. Forceps according to claim 1, wherein, during use of a clip the latch arm of which has a T-shaped profile, the distal end of said outer shaft is provided on each side with a rigid correspondingly-shaped plug which pushes on the T-arm of the clip arm profile.

11. Forceps according to claim 1, wherein said projection of said closing lever is provided with a ball end on the side facing the clip, the end engaging a corresponding distally open longitudinal groove in said other clip arm.

* * * * *